United States Patent [19]

White et al.

[11] 4,166,190

[45] Aug. 28, 1979

[54] PROCESS FOR THE PREPARATION OF METHACRYLIC ACID FROM METHACROLEIN

[75] Inventors: James F. White, Akron; James R. Rege, Shaker Heights; Robert K. Grasselli, Chagrin Falls; Dev D. Suresh, Warrensville Heights, all of Ohio

[73] Assignee: The Standard Oil Company, Cleveland, Ohio

[21] Appl. No.: 681,305

[22] Filed: Apr. 29, 1976

Related U.S. Application Data

[63] Continuation-in-part of Ser. No. 562,709, Mar. 27, 1975, Pat. No. 4,070,397, which is a continuation-in-part of Ser. No. 405,309, Oct. 11, 1973, Pat. No. 3,875,220.

[51] Int. Cl.$^2$ ............... C07C 51/32; C07C 57/04
[52] U.S. Cl. ..................... 562/534; 252/435; 252/437; 562/535
[58] Field of Search ............ 260/530 N; 252/435, 252/437; 562/534, 535

[56] References Cited

U.S. PATENT DOCUMENTS

| | | | |
|---|---|---|---|
| 3,875,220 | 4/1975 | White et al. | 260/530 N |
| 3,925,464 | 12/1975 | Ada et al. | 260/530 N |
| 3,976,688 | 8/1976 | Akiyama et al. | 260/530 N |
| 4,014,925 | 3/1977 | Ferlazzo et al. | 260/530 N |
| 4,042,625 | 8/1977 | Matsuzawa et al. | 260/530 N |
| 4,075,244 | 2/1978 | Akiyama et al. | 260/530 N |

FOREIGN PATENT DOCUMENTS

2448804  4/1975  Fed. Rep. of Germany ...... 260/530 N

*Primary Examiner*—Vivian Garner
*Attorney, Agent, or Firm*—Herbert C. Knudsen; Larry W. Evans

[57] ABSTRACT

Catalysts containing tungsten, phosphorus, vanadium, molybdenum, and promoted with at least one of the elements selected from the group selected from Sn, As, Cu, Ce, B, Cr, Fe, Ni, Co, U, Mn, Ag, Ru, Rh, Cd, Sr, In, Zn, and La have been found to be especially effective for the oxidation of unsaturated aldehydes to form the corresponding unsaturated acid.

8 Claims, No Drawings

PROCESS FOR THE PREPARATION OF METHACRYLIC ACID FROM METHACROLEIN

CROSS REFERENCE TO RELATED APPLICATION

This application is a continuation-in-part of the application filed by James F. White, James R. Rege, Robert K. Grasselli, and Dev D. Suresh, Ser. No. 562,709, and filed on Mar. 27, 1975, now U.S. Pat. No. 4,070,397 which is a continuation-in-part of the application filed by James F. White and James R. Rege, Ser. No. 405,309, filed on Oct. 11, 1973, and issued Apr. 1, 1975, as U.S. Pat. No. 3,875,220.

BACKGROUND OF THE INVENTION

A number of catalysts are known for the oxidation of unsaturated aldehydes to the corresponding acid. See, for example, U.S. Pat. No. 3,567,773. Although most of the disclosures suggest that the catalysts are useful for oxidizing methacrolein to methacrylic acid, it has been found that the yields of methacrylic acid are low and that special catalysts are required in this reaction.

U.S. Pat. No. 3,925,464 discloses a process for preparing unsaturated carboxylic acids which comprises reacting the corresponding unsaturated aldehydes with molecular oxygen in the presence of a catalyst consisting essentially of (a) molybdenum, (b) phosphorus, (c) at least one element selected from the group consisting of tungsten and magnesium, (d) at least one element selected from the group consisting of vanadium and bismuth, and (e) oxygen.

SUMMARY OF THE INVENTION

A process has now been discovered for the production of acrylic acid or methacrylic acid comprising reacting acrolein or methacrolein with molecular oxygen at a temperature of 200° to 600° C., in the presence of a catalyst and optionally in the presence of steam, the improvement comprising using a catalyst of the formula

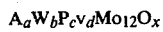
$$A_aW_bP_cV_dMo_{12}O_x$$

wherein
A is at least one of the elements selected from the group consisting of tin, arsenic, copper, cerium, boron, chromium, iron, nickel, cobalt, uranium, manganese, silver, rubidium, rhodium, cadmium, strontium, indium, zinc and lanthanum; and
a is about 0.1 to 6; b and d are about 0.1 to about 12; c is a positive number less than about 6; and
x is the number of oxygens required by the valence states of the other elements present.

The catalysts of the invention give high single pass yields to methacrylic acid and are very stable under the required operating conditions.

The central feature of the present invention is the catalyst. This catalyst is used in the known process for preparing unsaturated acids from the corresponding aldehydes. The catalysts may be any one of the catalysts designated by the formula above. The catalyst may be prepared by various techniques that are broadly described in the art and which are more fully taught by the present specification.

In the catalyst preparations, the various elements of the catalyst are combined, and the final product is dried normally at a temperature of about 100°–150° C. In some preparations, it is helpful to calcine the catalyst at an elevated temperature of about 300°–600° C., but such calcination is normally not required. A number of methods of combining the elements of the catalysts are known. The oxides of the elements could be combined in a slurry, and the resulting slurry refluxed and finally evaporated to form the catalyst. Alternative and preferred preparations involve the reflux of a solution of a soluble molybdenum, tungsten and vanadium compound, and then the addition of a phosphorus compound. The preferred preparations are those that give the best results in the Specific Embodiments below.

In the catalyst composition formula above, there are preferred ranges. Preferred are catalysts wherein the phosphorus is present in the range of about 0.5 to about 3, i.e., those catalysts wherein c is about 0.5 to about 3. Also preferred in the present invention are those catalysts which contain at least one of strontium, cadmium, uranium, cobalt, or chromium.

The catalyst of the invention may be used as pure active ingredients or it may be combined physically with a support material. A number of suitable supports are well known in the art. In an experimental study on supports, it was found that silica, zirconia, diatomaceous earth, titania and alumina supports generally tended to maintain the activity of the catalyst while silica gel and alumina gel tended to reduce the effectiveness of the catalysts. The catalysts of the present invention can be used with any of these support materials.

The catalysts of the invention may also be coated on a massive inert support. This coating technique is specifically shown in Examples 8–14. Broadly, this technique involves wetting a porous massive support with water to the extent that water does not remain on the surface of the massive support and then contacting a powder of the active catalytic material with the massive support while rotating the massive support in a container such as a simple glass jar. Coated catalysts have been found to be especially effective in this reaction to control the temperature of the reaction. As indicated above, the process of the invention wherein the unsaturated aldehyde is oxidized to the corresponding unsaturated acid is well known in the art. Broadly, the reaction involves a reactant feed of the unsaturated aldehyde and molecular oxygen over the catalyst. The reactant feed may also contain a diluent which is normally steam. The ratio of the reactants in the feed may vary widely. Normally about 0.2 to about 4 moles of molecular oxygen are present per mole of the unsaturated aldehyde. The amount of diluent employed may also vary widely, but normally falls within the range of about 1 to about 10 moles of diluent per mole of the unsaturated aldehyde.

As noted above, the reaction is normally conducted at a reaction temperature of 200° to 600° C., with temperatures of about 300° to 400° C. being of special interest. The reaction can be conducted under subatmospheric, superatomospheric or atmospheric pressures at a contact time ranging from a fraction of a second to ten seconds or more. Reaction can be conducted in a fluid bed or more commonly in a fixed bed reactor.

As noted, the process of the invention is related to the preparation of acrylic acid or methacrylic acid from the corresponding unsaturated aldehyde. Of special interest in the invention is the production of methacrylic acid from methacrolein because of the very high yields obtained and the small amounts of by-products formed.

SPECIFIC EMBODIMENTS

EXAMPLES 1-7

Production of methacrylic acid from methacrolein

Various catalysts of the invention were prepared as described below and tested in the oxidation of methacrolein to methacrylic acid.

EXAMPLES 1 & 2

$W_{0.8}P_{1.3}V_2Mo_{12}O_x$

An aqueous slurry containing 86.2 g. $MoO_3$, 7.7g. of 85% $H_3PO_4$, 7.5 g. $V_2O_3$ and 10.8 g. ammonium paratungstate was prepared. The slurry was refluxed overnight, evaporated and dried at 120° C. overnight.

EXAMPLES 3 & 4

$W_3P_{1.5}V_3Mo_{12}O_x$

An aqueous solution of 11.5 g. 85% $H_3PO_4$, 141.2 g. $(NH_4)_6Mo_7O_{24}.4H_2O$, and 53.9 g. of $(NH_4)_6W_7O_{24}.2H_2O$ in 1500 ml. of water. To this solution was added 23.4 g. of $NH_4VO_3$. The resulting slurry was deep red and on a continued heating became orange. The resulting slurry was deep red and on a continued heating became orange. The resulting mixture was evaporated and dried at 120° C. overnight.

EXAMPLE 5

$W_{1.2}PV_3Mo_{12}O_x$

A solution of 17.6 g. $NH_4VO_3$ dissolved in one liter of water was prepared. To this solution was added 105.7 g. $(NH_4)_6Mo_7O_{24}.4H_2O$, and the mixture was heated with stirring until the solid was dissolved. To the resulting solution 5.76 g. of 85% $H_3PO_4$ was added, and the solution turned red. To this mixture was added 16.2 g. ammonium paratungstate and all solids appeared to be dissolved. The catalyst was evaporated to dryness, and the resulting solid was dried at 110° C. overnight. The solid was ground and screened to a size of 20 to 30 U.S. Standard mesh, and the screened solid was heated at 430° C. for two hours.

EXAMPLE 6

$W_{1.2}P_2V_3Mo_{12}O_x$

The preparation of Example 5 was followed except that 11.52 g. of 85% $H_3PO_4$ was added rather than 5.76 g.

EXAMPLE 7

$W_{1.2}P_3V_3Mo_{12}O_x$

The preparation of Example 5 was followed except that 17.30 g. of 85% $H_3PO_4$ was added rather than 5.76 g.

A reactor was constructed of a 1 cm. inside diameter stainless steel tube having a reaction zone of 20 cc. A mixture of methacrolein, air and steam was fed over the catalyst in a ratio of 1/6.3/5.2 at the temperature and apparatus contact time shown in the Table. The compositions of these catalysts and the results using these catalysts are shown in Table I. The results are stated as follows:

$$\% \text{ single pass yield} = \frac{\text{moles of product formed} \times 100}{\text{moles of methacrolein fed}}$$

$$\% \text{ conversion} = \frac{\text{moles of methacrolein reacted} \times 100}{\text{moles of methacrolein fed}}$$

$$\% \text{ selectivity} = \frac{\text{moles of methacrylic acid formed} \times 100}{\text{moles of methacrolein reacted}}$$

Table 1

Oxidation of Methacrolein to Methacrylic Acid Using Catalysts Containing WPVMo

| | | | | Results, % | | | |
|---|---|---|---|---|---|---|---|
| | | Reaction Temp., | C.T., | Single Pass Yield, Acid | | | |
| Example | Catalyst | °C. | Sec. | Methacrylic | Acrylic | Conversion | Selectivity |
| 1 | $W_{0.8}P_{1.3}V_2Mo_{12}O_x$ | 385 | 4.6 | 12.7 | 14.6 | 70.6 | 18.0 |
| 2 | " | 355 | 4.8 | 29.9 | 0.0 | 65.9 | 45.4 |
| 3 | $W_3P_{1.5}V_3Mo_{12}O_x$ | 365 | 4.8 | 53.2 | 2.5 | 82.9 | 64.2 |
| 4 | " | 335 | 5.0 | 53.4 | 2.6 | 75.3 | 70.9 |
| 5 | $W_{1.2}PV_3Mo_{12}O_x$ | 355 | 4.8 | 17.1 | 2.1 | 48.4 | 35.3 |
| 6 | $W_{1.2}P_2V_3Mo_{12}O_x$ | 385 | 4.5 | 26.9 | 3.7 | 70.0 | 38.4 |
| 7 | $W_{1.2}P_3V_3Mo_{12}O_x$ | 355 | 4.7 | 27.2 | 3.0 | 60.3 | 45.1 |

EXAMPLES 8-14

Active catalytic material coated on a support

An active catalytic material having the formula $W_3P_2V_2Mo_{12}O_x$ was prepared by dissolving 706.26 g. of $(NH_4)_6Mo_7O_{24}.4H_2O$, 280.91 g. $(NH_4)_6W_4O_{24}.8H_2O$ and 78.00 g. $NH_4VO_3$ in 3 liters of boiling distilled water. After three hours, the boiling was discontinued and stirring was continued over the weekend. To the resulting solution was then added 76.86 g. of 85% $H_3PO_4$, the mixture was boiled down and the solid dried at 110° C. and calcined at 415° C. for one hour.

This active catalytic powder was coated on Alundum particles sold at Norton SA-5209. The particles were placed in a glass jar and wetted with water. The water content was reduced to 2.4 g./25 g. of particles with the flow of air from a hot air gun. The active catalytic powder was ground to a size of less than 50 U.S. Standard mesh. While the glass jar was rotated on an angle about 17 g. of active powder per 25 g. of Alundum was added in five separate portions. Between each addition, the rotation of the jar was continued from 15-45 minutes. The catalyst produced was an Alundum support with a strongly adhering coat of active catalytic material. The catalyst was then dried in an oven at 110° C. over the weekend. The resulting catalyst was 39.8% $W_3P_2V_2Mo_{12}O_x$ and 60.2% Alundum. In the same manner, a coated catalyst containing 34.8% $W_3P_2V_2Mo_{12}O_x$ and 65.2% Alundum sold as Norton SA-203 and a catalyst containing 20.4% $W_3P_2V_2Mo_{12}O_x$ and 79.6% Alundum SA-203 were also prepared. Using the same reactor and feed as shown above, these catalysts were tested in the production of methacrylic acid from methacrolein. The results are shown in Table 2.

Table 2
Production of Methacrylic Acid Using $W_3P_2V_2Mo_{12}O_x$ alone and in Coated Form

| Example | Catalyst | Reaction Temp., °C. | C.T., Sec. | Single Pass Yield Methacrylic Acid | Conversion | Selectivity |
|---|---|---|---|---|---|---|
| 8 | Active only | 360 | 2.6 | 68.9 | 92.5 | 74.5 |
| 9 | " | " | 2.5 | 67.5 | 93.5 | 72.2 |
| 10 | 39.8% Active 60.2% Alundum | 380 | 4.4 | 65.2 | 93.3 | 69.9 |
| 11 | " | 365 | 4.6 | 59.4 | 85.7 | 69.3 |
| 12 | 34.8% Active 65.2% Alundum | 360 | 4.7 | 66.2 | 92.3 | 71.7 |
| 13 | 20.4% Active 79.6% Alundum | 370 | 4.6 | 65.5 | 86.4 | 75.8 |
| 14 | " | 390 | 4.5 | 64.1 | 92.2 | 69.5 |

EXAMPLE 15

Catalysts of the invention containing optional elements

Various catalysts of the invention containing different elements were prepared as shown below.

EXAMPLE 15

$Rb_{0.75}W_3P_{1.5}V_{2.25}Mo_{12}O_x$

A solution of 141.2 g. $(NH_4)_6Mo_7O_{24}.4H_2O$ and 11.52 g. 85% $H_3PO_4$ in 2 liters of water was prepared. To this solution was added 53.9 g. of $(NH_4)_6W_7O_{24}.2H_2O$ and then 17.6 g. of $NH_4VO_3$. To this mixture was then added 7.2g. of $RbC_2H_3O_2$. The mixture was boiled dry, and the solid was dried at 110° C. overnight.

EXAMPLE 16

$Sn_{0.5}Cu_2W_{1.2}PV_3Mo_{12}O_x$

A slurry was prepared by the addition to 800 ml. of water 72.0 g. of $MoO_3$, 11.36 g. $V_2O_5$, 3.13 g. $SnO_2$ and 5.65 g. 85% $H_3PO_4$. The slurry was heated to reflux with stirring overnight. To the slurry was then added 9.19 g. of finely divided tungsten metal and after two hours of reflux 16.63 g. of cupric acetate was added and refluxing continued for 1.5 hours. The slurry was evaporated to dryness and dried at 110° C. overnight.

EXAMPLES 17 AND 18

33.3% $Sn_{0.5}Cu_2W_{1.2}PV_3Mo_{12}O_x$ and 66.7% Alundum

The active catalyst of Example 16 was coated according to the procedure shown in Examples 8-14 to obtain a catalyst having ⅓ active catalytic material and ⅔ Alundum.

EXAMPLES 19 AND 20

$Sn_{0.5}Cu_2W_{1.2}P_2V_3Mo_{12}O_x$

The procedure of Example 16 was repeated except that twice the amount of $H_3PO_4$ was used.

EXAMPLE 21

$SbW_3P_2V_2Mo_{12}O_x$

A solution was prepared using 500 mls. of water and sequentially dissolving therein 88.3 g. of $(NH_4)_6Mo_7O_{24}.4H_2O$, 35.1 g. $(NH_4)_6W_4O_{13}.8H_2O$ and 9.7 g. $NH_4VO_3$. The solution was boiled for five hours and allowed to stand overnight with continuous stirring. To the cool solution was added 9.6 g. of 85%$H_3PO_4$. After about one hour of stirring, heating was resumed. To this hot solution was added 6.05 g. $Sb_2O_3$. The mixture was boiled dry, and the solid was dried in an oven over the weekend.

EXAMPLES 22-32

The catalysts were prepared in the same manner as Example 21 to give catalysts of $M_1W_3P_2V_2Mo_{12}O_x$ (except for rhodium catalyst which used $Rh_{0.25}$, and iron which was $Fe_2$) by adding the appropriate amounts of the following chemicals in each preparation rather than the antimony compound: $Bi_2O_3$, $Ni_2O_3$; $Cr(C_2H_3O_2).H_2O$; $Co(C_2H_3O_2)_2.4H_2O$; $RhCl_3.3H_2O$; $Cd(C_2H_3O_2)_2.2H_2O$; $Fe(NO_3)_3.9H_2O$; $AgC_2H_3O_2$; $Sr(OH)_2.8H_2O$; $UO_2(C_2H_3O_2)_2.2H_2O$; $Ce(C_2H_3O_2)_3.1.5H_2O$.

These catalysts were employed in the production of methacrylic acid in the manner shown above, and the results of these experiments are shown in Table 3.

Table 3
Production of Methacrylic Acid Using Catalysts of the Invention Containing Optional Elements

| Example | Catalyst | Optional Element(s) | Temp., °C. | C.T., Sec. | Single Pass Yield of Methacrylic Acid | Conversion | Selectivity |
|---|---|---|---|---|---|---|---|
| 15 | $Rb_{0.75}W_3P_{1.5}V_{2.25}Mo_{12}O_x$ | Rb | 370 | 4.6 | 47.2 | 89.0 | 53.0 |
| 16 | $Sn_{0.5}Cu_2W_{1.2}PV_3Mo_{12}O_x$ | SnCu | 355 | 4.6 | 17.4 | 57.0 | 30.5 |
| 17 | 33.3% Active of Ex. 16 66.7% Alundum | " | 390 | 4.4 | 27.1 | 63.2 | 42.9 |
| 18 | " | " | 365 | 4.6 | 23.4 | 60.7 | 38.6 |
| 19 | $Sn_{0.5}Cu_2W_{1.2}P_2V_3Mo_{12}O_x$ | " | 390 | 4.4 | 21.6 | 67.4 | 32.3 |
| 20 | " | " | 360 | 4.6 | 20.5 | 63.3 | 32.4 |
| 21 | $Sb_1W_3P_2V_2Mo_{12}O_x$ | Sb | " | 2.6 | 68.5 | 93.8 | 73.0 |
| 22 | $BiW_3P_2V_2Mo_{12}O_x$ | Bi | 370 | 4.6 | 61.1 | 96.0 | 63.6 |
| 23 | $NiW_3P_2V_2Mo_{12}O_x$ | Ni | 380 | 2.6 | 61.1 | 96.1 | 64.1 |
| 24 | $CrW_3P_2V_2Mo_{12}O_x$ | Cr | 405 | 2.4 | 47.0 | 82.8 | 56.8 |
| 25 | $CoW_3P_2V_2Mo_{12}O_x$ | Co | 435 | 2.3 | 46.2 | 83.2 | 55.5 |
| 26 | $Rh_{0.25}W_3P_2V_2Mo_{12}O_x$ | Rh | 385 | 2.6 | 19.9 | 64.5 | 30.9 |
| 27 | $CdW_3P_2V_2Mo_{12}O_x$ | Cd | 365 | " | 63.5 | 89.6 | 70.9 |

Table 3-continued

Production of Methacrylic Acid Using Catalysts of the Invention Containing Optional Elements

| Example | Catalyst | Optional Element(s) | Temp., °C. | C.T., Sec. | Single Pass Yield of Methacrylic Acid | Conversion | Selectivity |
|---|---|---|---|---|---|---|---|
| 28 | $Fe_2W_3P_2V_2Mo_{12}O_x$ | Fe | 455 | 2.3 | 17.5 | 58.4 | 30.0 |
| 29 | $AgW_3P_2V_2Mo_{12}O_x$ | Ag | 350 | 2.6 | 42.7 | 57.7 | 74.0 |
| 30 | $UW_3P_2V_2Mo_{12}O_x$ | U | 380 | 2.5 | 57.5 | 91.1 | 63.1 |
| 31 | $SrW_3P_2V_2Mo_{12}O_x$ | Sr | 390 | " | 55.0 | 91.4 | 60.2 |
| 32 | $CeW_3P_2V_2Mo_{12}O_x$ | Ce | 425 | 2.4 | 39.8 | 81.3 | 48.9 |

We claim:

1. In a process for the production of methacrylic acid comprising reacting methacrolein with molecular oxygen at a temperature of 200° C. to 600° C. in the presence of a catalyst and optionally in the presence of steam, the improvement comprising using as a catalyst a catalyst consisting essentially of a catalytic oxide of tungsten, phosphorus, vanadium, molybdenum and at least one element selected from the group consisting of cobalt, rhodium, cadmium, strontium, indium and zinc, the catalyst composition having the formula $A_aW_bP_cV_dMo_{12}O_x$ wherein A is at least one element selected from the group consisting of cobalt, rhodium, cadmium, strontium, indium and zinc; and wherein a is about 0.1–6; b and d are about 0.1 to about 12; c is a positive number less than 6; and x is the number of oxygens required by the valence states of the other elements present.

2. The process of claim 1 wherein A is at least one element selected from the group consisting of strontium, cadmium and cobalt.

3. The process of claim 1 wherein c is about 0.5 to about 3.

4. The process of claim 1 wherein A is cadmium.

5. The process of claim 1 wherein A is strontium.

6. The process of claim 1 wherein A is cobalt.

7. The process of claim 1 wherein the catalyst is $Cd_1W_3P_2V_2Mo_{12}O_x$.

8. The process of claim 1 wherein A is rhodium.

* * * * *